(12) United States Patent
Yun et al.

(10) Patent No.: US 10,383,588 B2
(45) Date of Patent: Aug. 20, 2019

(54) GANTRY OF COMPUTED TOMOGRAPHY (CT) APPARATUS

(71) Applicant: Samsung Electronics Co., Ltd, Gyeonggi-do (KR)

(72) Inventors: Alexander Yun, Seoul (KR); Sung Ki Kim, Seoul (KR); Vikram Dave, Gyeonggi-do (KR)

(73) Assignee: Samsung Electronics Co., Ltd., Suwon-si (KR)

(*) Notice: Subject to any disclaimer, the term of this patent is extended or adjusted under 35 U.S.C. 154(b) by 284 days.

(21) Appl. No.: 15/582,417

(22) Filed: Apr. 28, 2017

(65) Prior Publication Data

US 2017/0325764 A1 Nov. 16, 2017

(30) Foreign Application Priority Data

May 16, 2016 (KR) .......................... 10-2016-0059771

(51) Int. Cl.
*A61B 6/03* (2006.01)
*A61B 6/00* (2006.01)

(52) U.S. Cl.
CPC ............ *A61B 6/4476* (2013.01); *A61B 6/035* (2013.01); *A61B 6/4435* (2013.01)

(58) Field of Classification Search
CPC ....... A61B 6/4476; A61B 6/032; A61B 6/035; A61B 6/4435

USPC ...................................................... 378/4–20
See application file for complete search history.

(56) References Cited

U.S. PATENT DOCUMENTS

| 5,703,921 | A | * | 12/1997 | Fujita | ..................... | A61B 6/035 |
| | | | | | | 378/15 |
| 7,014,361 | B1 | | 3/2006 | Ein-Gal | | |
| 2013/0077737 | A1 | | 3/2013 | Fasoli | | |

FOREIGN PATENT DOCUMENTS

| DE | 102013227060 A1 * | 6/2015 | ............ A61B 6/035 |
| KR | 101254098 B1 | 4/2013 | |
| KR | 1020150073858 A | 7/2015 | |

* cited by examiner

*Primary Examiner* — Courtney D Thomas

(57) ABSTRACT

A gantry of a computed tomography (CT) apparatus includes a rotating frame configured to rotate around a rotation axis and a rotation driver configured to rotate the rotating frame. The gantry also includes a stator configured to support the rotating frame while the rotating frame rotates and electronic components arranged along a circumferential direction of the rotating frame. The rotating frame includes a plurality of annular frames positioned concentrically around the rotation axis and a plurality of rib frames arranged on circumferential surfaces of the plurality of annular frames and parallel to the rotation axis in such a manner as to connect the plurality of annular frames. At least one of the plurality of annular frames and the plurality of rib frames has a recessed portion along a longitudinal direction thereof.

20 Claims, 15 Drawing Sheets

(a)

(a)

GANTRY OF COMPUTED TOMOGRAPHY (CT) APPARATUS

CROSS-REFERENCE TO RELATED APPLICATION(S) AND CLAIM OF PRIORITY

The present application is related to and claims the benefit of Korean Patent Application No. 10-2016-0059771, filed on May 16, 2016, in the Korean Intellectual Property Office, the disclosure of which is incorporated herein in its entirety by reference.

TECHNICAL FIELD

The present disclosure relates to a gantry of a computed tomography (CT) apparatus, and in particular, to a rotating frame of the gantry.

BACKGROUND

Medical imaging apparatuses are used to obtain images showing an internal structure of an object.

A computed tomography (CT) apparatus is a representative example of the medical imaging apparatuses. The CT apparatus may provide a cross-sectional image of an object by transmitting X-rays through an object.

When X-rays are passed through the object from multiple directions, electronic components such as an X-ray generator and an X-ray detector may rotate around the object. The electronic components may be mounted on a rotating frame of a gantry, and the gantry may further include a stator that is affixed to the ground to support the rotating frame while the rotating frame rotates.

SUMMARY

A rotating frame of a conventional gantry is bulky and has a structure that is difficult to manufacture and maintain. In particular, the conventional gantry having a semi-closed structure suffers from a low cooling efficiency due to restriction in airflow for ventilation and generates high levels of noise.

To address the above-discussed deficiencies, it is a primary object to provide a rotating frame of a gantry having a new structure capable of overcoming the above limitations of conventional technology.

Additional aspects will be set forth in part in the description which follows and, in part, will be apparent from the description, or may be learned by practice of the presented embodiments.

According to an aspect of an embodiment, a gantry of a computed tomography (CT) apparatus includes: a rotating frame configured to rotate around a rotation axis; a rotation driver configured to rotate the rotating frame; a stator configured to support the rotating frame while the rotating frame rotates; and electronic components arranged along a circumferential direction of the rotating frame. The rotating frame includes a plurality of annular frames positioned concentrically around the rotation axis and a plurality of rib frames arranged on circumferential surfaces of the plurality of annular frames and parallel to the rotation axis in such a manner as to connect the plurality of annular frames. At least one of the plurality of annular frames and the plurality of rib frames has a recessed portion along a longitudinal direction thereof.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

Figure 1:
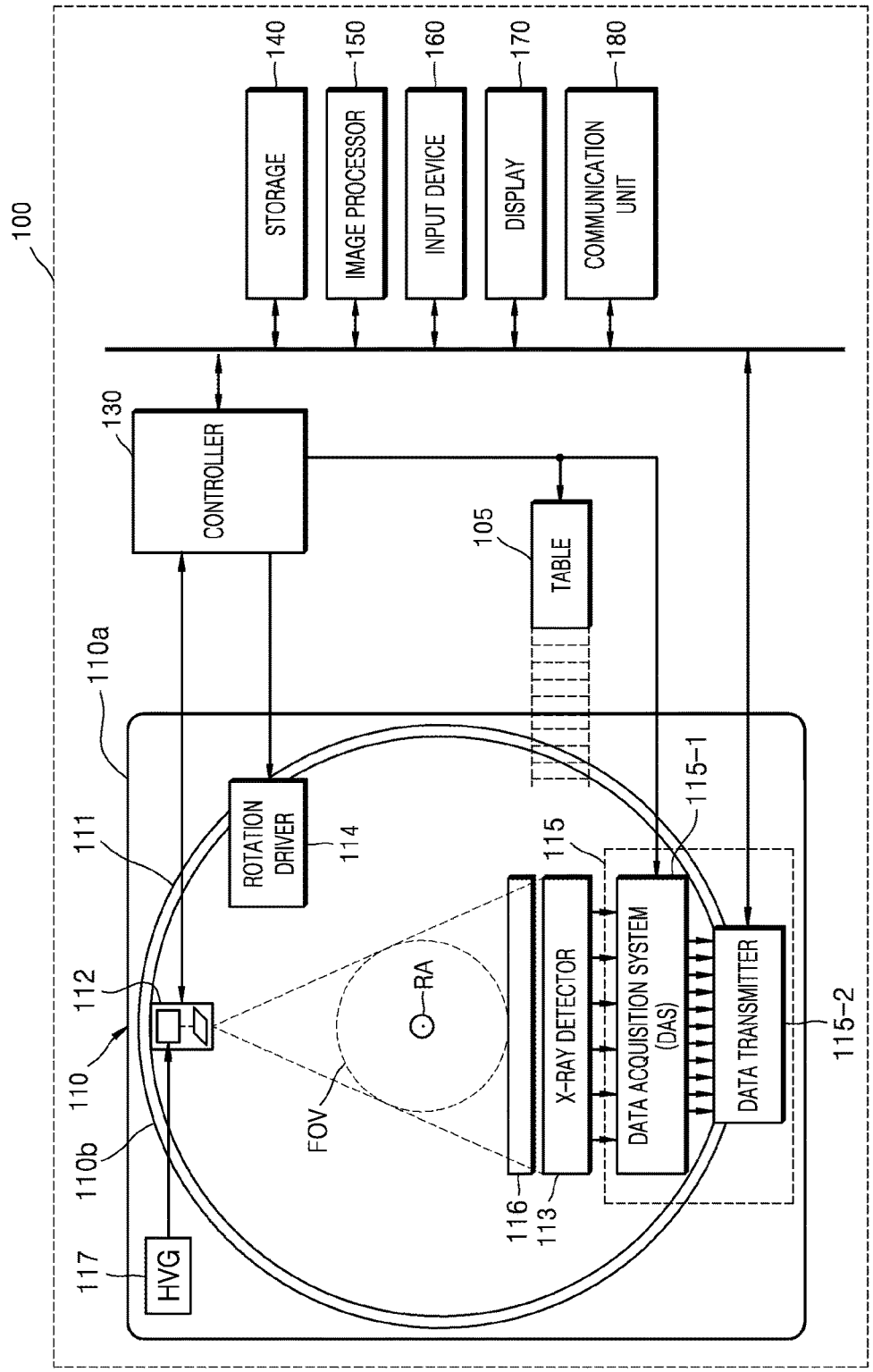
FIG. 1 illustrates a structure of a computed tomography (CT) system according to an embodiment.

FIGS. 1 through 9B, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged medical imaging apparatus.

The present specification describes principles of the present disclosure and sets forth embodiments thereof to clarify the scope of the present disclosure and to allow those of ordinary skill in the art to implement the embodiments. The present embodiments may have different forms and should not be construed as being limited to the descriptions set forth herein.

Like reference numerals refer to like elements throughout. The present specification does not describe all components in the embodiments, and common knowledge in the art or the same descriptions of the embodiments will be omitted below. The term "part" or "portion" used herein may be implemented using hardware or software, and according to embodiments, a plurality of "parts" or "portions" may be formed as a single unit or element, or one "part" or "portion" may include a plurality of units or elements. Expressions such as "at least one of," when preceding a list of elements, modify the entire list of elements and do not modify the individual elements of the list. Hereinafter, the operating principles and embodiments of the present disclosure will be described in detail with reference to the accompanying drawings.

In the present specification, an image may include a medical image obtained by a computed tomography (CT) apparatus, a magnetic resonance imaging (MRI) apparatus, an ultrasound imaging apparatus, an X-ray apparatus, or another medical imaging apparatus.

Furthermore, in the present specification, an "object" may be a target to be imaged and include a human, an animal, or a part of a human or animal. For example, the object may include a body part (an organ, etc.) or a phantom.

Furthermore, in the present specification, a 'CT system,' or 'CT apparatus' refers to a system or apparatus configured to emit X-rays while rotating around at least one axis relative to an object and photographing the object by detecting the X-rays.

In addition, a 'CT image' means an image reconstructed from raw data acquired by photographing an object through detecting X-rays that are emitted as the CT system or apparatus rotates about at least one axis with respect to the object.

FIG. 1 illustrates a structure of a CT system 100 according to an embodiment.

Referring to FIG. 1, the CT system 100 according to the present embodiment may include a gantry 110, a table 105, a controller 130, a storage 140, an image processor 150, an input device 160, a display 170, and a communication unit 180.

The gantry 110 may include a rotating frame 111, an X-ray generator 112, an X-ray detector 113, a rotation driver 114, and a readout device 115. Furthermore, the gantry 110 includes a rotor rotating around an axis and a stator supporting the rotor.

The rotor may include the rotating frame 111, the X-ray generator 112, and the X-ray detector 113. The rotating frame 111 rotates around a predetermined rotation axis (RA) and may, for example, have a cylindrical or ring shape. According to control by the controller 130, the rotation driver 114 induces or creates a driving force for rotating the rotating frame 111 by using a motor, etc. As the rotating frame 111 rotates, the X-ray generator 112 and the X-ray detector 113 may rotate along a circumferential direction of the rotating frame 111. In addition, the rotor may include a slip ring that is in contact with the rotating frame 111 to transfer a signal or power The stator 110a may support the rotor 110b while the rotor rotates. The stator may include a support frame touching the ground and a cover frame covering at least a part of the rotor. In this case, bearings are provided between the cover frame and the rotor to minimize a frictional force so that the rotor is free to rotate. For example, the bearings may be ball bearings or magnetic bearings.

X-ray radiation that reaches the X-ray detector 113 includes not only attenuated primary radiation that forms an image but also scattered radiation that deteriorates the quality of an image. An anti-scatter grid 116 may be positioned between an object and the X-ray detector 113 to transmit most of the primary radiation and attenuate the scattered radiation, thereby improving the quality of acquired medical imaging data.

The object may be positioned on the table 105, which may move, tilt, or rotate during a CT scan.

The X-ray generator 112 may receive a voltage and a current from a power distribution unit (PDU) (not shown) via the slip ring and then a high voltage generator (HVG) 117 to generate and emit X-rays. For example, the X-rays emitted by the X-ray generator 112 may be shaped as a cone beam or a parallel beam. [A1]

The CT system 100 may be implemented as a single-source CT system including one X-ray generator 112 and one X-ray detector 113 or a dual-source CT system including two X-ray generators 112 and two X-ray detectors 113.

The X-ray detector 113 detects radiation that has passed through the object. For example, the X-ray detector 113 may detect radiation by using a scintillator, a photon counting detector, etc.

Methods of driving the X-ray generator 112 and the X-ray detector 113 may vary depending on scan modes used for scanning of the object. The scan modes are divided into an axial scan mode and a helical scan mode according to a path along which the X-ray detector 113 moves. Furthermore, the scan modes are divided into a prospective mode and a retrospective mode according to a time interval during which X-ray radiation is emitted.

The controller 130 may control an operation of each of the components in the CT system 100. The controller 130 may include a memory configured to store program code or data for performing control and a processor configured to process the program code or data. The controller 130 may be implemented in various combinations of at least one memory and at least one processor. The processor may generate or delete a program module according to an operating status of the CT system 100 and process operations of the program module.

The readout device 115 receives a detection signal generated by the X-ray detector 113 and outputs the detection signal to the image processor 150. The readout device 115 may include a data acquisition system (DAS) 115-1 and a data transmitter 115-2. The DAS 115-1 uses at least one amplifying circuit to amplify a signal output from the X-ray detector 113 and outputs the amplified signal. The data transmitter 115-2 uses a circuit such as a multiplexer MUX to output the signal amplified in the DAS 115-1 to the image processor 150. According to a slice thickness or the number of slices, only some data collected by the X-ray detector 113 may be provided to the image processor 150.

The image processor 150 generates tomography data based on a signal acquired by the readout device 115 (e.g., raw data that is data before being processed). The image processor 150 may pre-process a generated signal, convert the generated signal into tomography data, and post-process the tomography data. The image processor 150 may perform some or all of the processes described herein, and the type or order of processes performed by the image processor 150 may vary according to embodiments.

According to embodiments, the image processor 150 may perform some or all of the processes for reconstructing a tomography image to generate the tomography data. According to an embodiment, the tomography data may be in the form of data that has undergone filtered back-projection (FBP) or a tomography image. According to embodiments, additional processing may be performed on the tomography data by an external device such as a server, a medical apparatus, or a portable device.

Raw data is a set of data values corresponding to intensities of radiation that has passed through the object and may include projection data or a sinogram. Back-projected data is obtained after performing back-projection on raw data by using information about an angle at which radiation is emitted. A tomography image is obtained by using image reconstruction techniques including back-projection of the raw data.

The storage 140 is a storage medium for storing control-related data, image data, etc., and may include a volatile or non-volatile storage medium.

The input device 160 receives control signals, data, etc., from a user. For example, the control signals may include a control signal for controlling a scanning operation, a control signal for controlling a display of a medical image, etc.

The display 170 may display information indicating an operating status of the CT system 100, medical information, medical image data, etc.

The CT system 100 includes the communication unit 180 and may be connected to external devices such as a server, a medical apparatus, and a portable device (a smart phone, a tablet PC, a wearable device, etc.) via the communication unit 180.

The communication unit 180 may include at least one component that enables communication with an external device. For example, the communication unit 180 may include at least one of a local area communication module, a wired communication module, and a wireless communication module.

Furthermore, the communication unit 180 may receive control signals and data from an external device and transmit the received control signals to the controller 130 so that the controller 130 may control the CT system 100 according to the received control signals.

Alternatively, by transmitting a control signal to an external device via the communication unit 180, the controller 130 may control the external device according to the control signal.

For example, the external device may process data according to a control signal received from the controller 130 via the communication unit 180.

A program for controlling the CT system 100 may be installed on the external device and may include instructions for performing some or all of the operations of the controller 130.

The program may be preinstalled on the external device, or a user of the external device may download the program from a server providing an application for installation. The server for providing an application may include a recording medium having the program recorded thereon.

According to embodiments, the CT system 100 may use contrast media or not during a CT scan, and may be implemented as a device connected to other equipment.

FIGS. 2A through 2C and FIGS. 3A through 3C illustrate rotating frames (e.g., 111 of FIG. 1) as a part of the gantry (110 of FIG. 1) and electronic components arranged on the rotating frames, according to embodiments.

In this case, the rotating frame 111 may be driven by the rotation driver 114 included in the gantry 110 to rotate, and the stator of the gantry 110 may support the rotating frame 111 while the rotating frame 111 rotates.

Referring to FIGS. 2A through 2C and 3A through 3C, rotating frames 200 and 300 corresponding to the rotating frame 111 of FIG. 1 may each include a plurality of annular frames and a plurality of rib frames arranged along a rotation axis Z. In this case, arrangement of the plurality of rib frames along the rotation axis Z may include arranging the plurality of rib frames substantially parallel to the rotation axis Z. At least one of the annular frames and the rib frames may have a recessed shape along a longitudinal direction thereof. For example, a height of a frame may be in a range of between 25 mm and 80 mm. Furthermore, a cover (not shown) may be provided to surround at least one of the annular frames and the rib frames.

The rib frames may be positioned on circumferential surfaces of the annular frames in such a manner as to connect the annular frames.

In this case, 'the rib frames connecting the annular frames' may mean that the rib frames affixes the annular frames by connecting them together, or that the rib frames are provided on the circumferential surfaces of the annular frames to interconnect the annular frames while not substantially affixing them.

Furthermore, 'the rib frames being positioned on the circumferential surfaces' may mean that the rib frames may be positioned in close contact with the circumferential surfaces of the annular frames, or that the rib frames are engaged with the annular frames with an engagement reinforcing member or surface protecting member such as a washer interposed therebetween.

Furthermore, electronic components may be positioned on surfaces of the rib frames. Similarly, 'the electronic components being positioned on surfaces of the rib frames' may mean that the electronic components may be positioned in close contact with the surfaces of the rib frames, or that the rib frames are engaged with the electronic components with an engagement reinforcing member or surface protecting member such as a washer interposed therebetween.

Figure 2A:
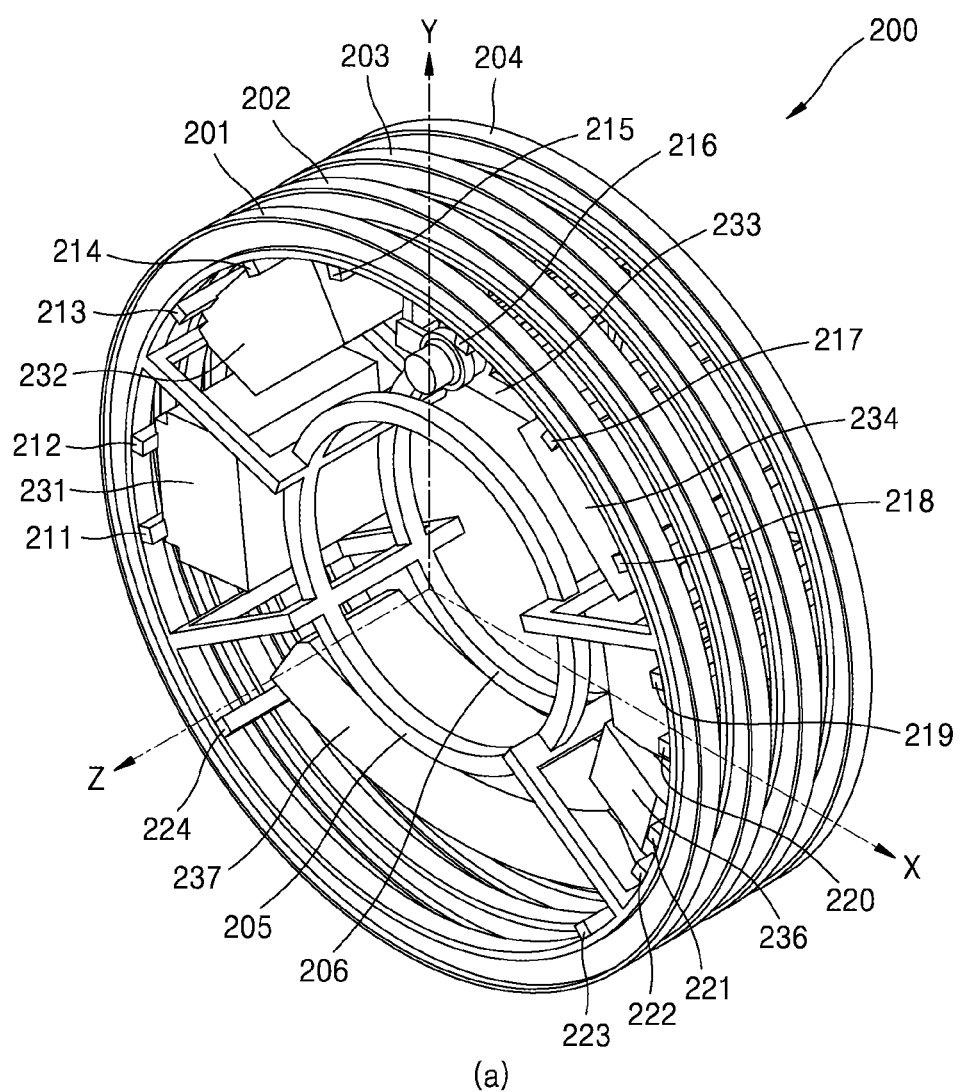
FIGS. 2A through 2C and FIGS. 3A through 3C illustrate rotating frames on which electronic components are arranged, according to embodiments.
Figure 2B:
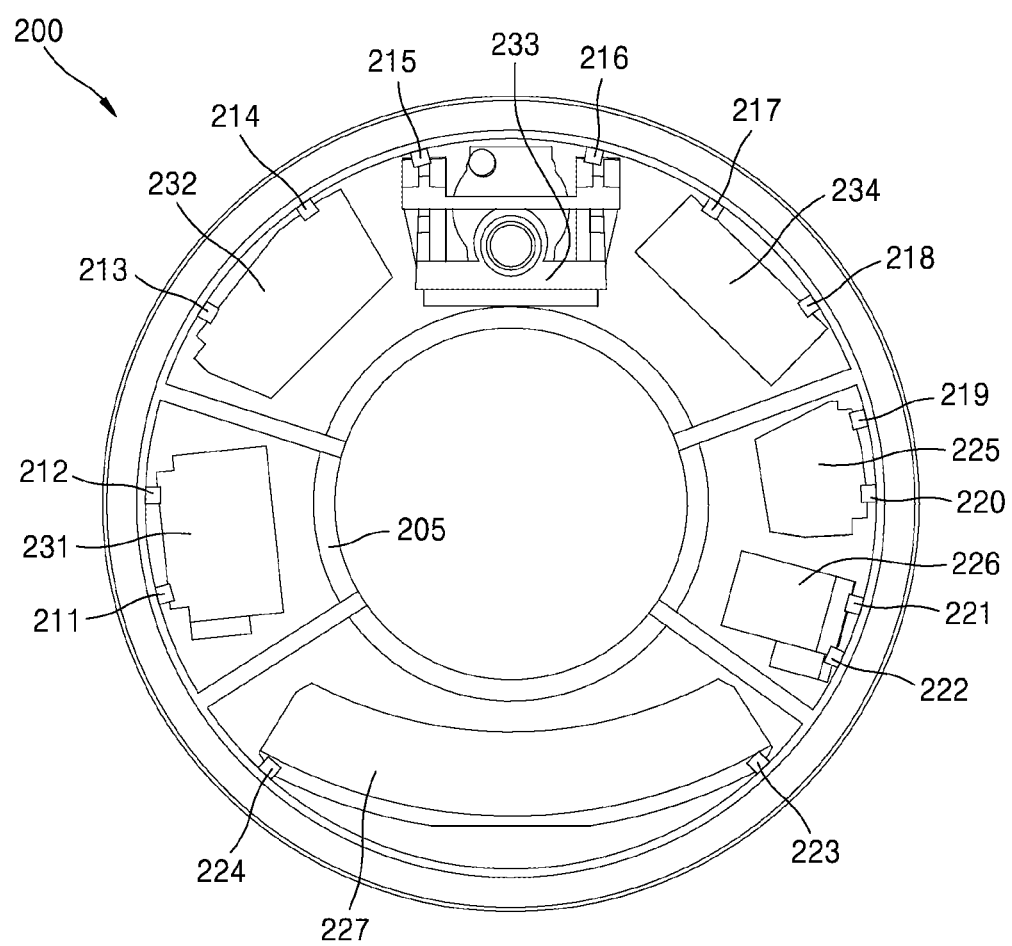
Figure 2C:
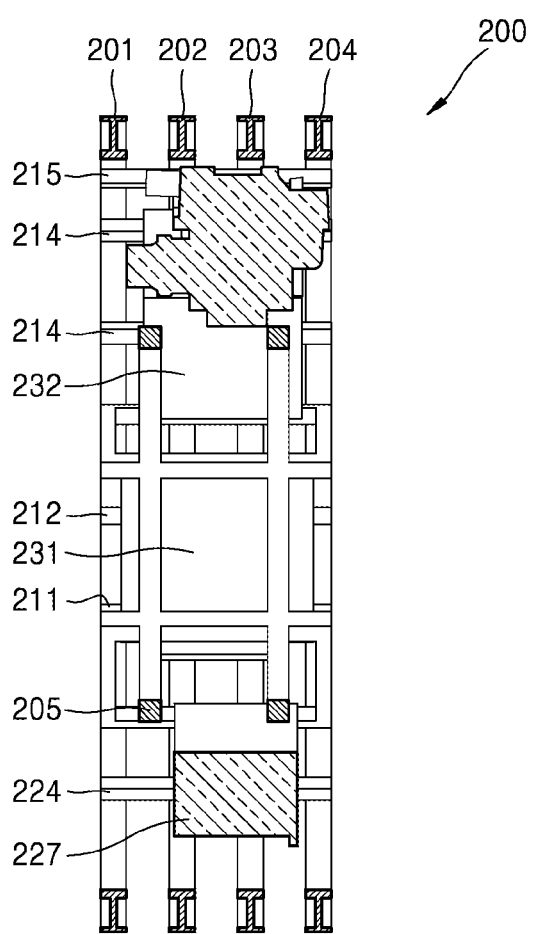

FIGS. 2A through 2C illustrate the rotating frame 200 having electronic components 231 through 237 mounted thereto as an example of the rotating frame 111 of FIG. 1. FIGS. 2A through 2C respectively illustrate a perspective view, a front view, and a side view of the rotating frame 200.

Referring to FIGS. 2A through 2C, the rotating frame 200 may include a plurality of outer annular frames 201 through 204, a plurality of inner annular frames 205 and 206, and a plurality of rib frames 211 through 224. The plurality of outer annular frames 201 through 204 may have a diameter that is greater than that of the plurality of inner annular frames 205 and 206 close to the rotation axis Z. Thus, the electronic components 231 through 237 may be provided within spaces between the outer annular frames 201 through 204 and the inner annular frames 205 and 206.

Furthermore, the rib frames 211 through 224 may be positioned on circumferential surfaces, which are oriented toward a center located on the rotation axis Z, among surfaces of the outer annular frames 201 through 204. The rib frames 211 through 224 may be located on the circumferential surfaces at equally spaced intervals or in consideration of positions where the electronic components 231 through 237 are installed. In this case, the electronic components 231 through 237 may be fixedly mounted on surfaces of the rib frames 211 through 224 connecting the outer annular frames 201 through 204.

Furthermore, the rib frames 211 through 224 may be arranged on the circumferential surfaces of the outer annular frames 201 through 204, based on sizes and weights of the electronic components 231 through 237. For example, as the sizes or weights of the electronic components 231 through 237 increase, the number of the rib frames 211 through 224 for supporting the electronic components 231 through 237 may increase.

In addition, to minimize vibration of the gantry 110 while the rotating frame 200 rotates, the electronic components 231 through 237 may be arranged evenly along a circumferential direction of the outer annular frames 201 through 204. In other words, the electronic components 231 through 237 may be arranged along the circumferential direction of the outer annular frames 201 through 204 so that a center of gravity of the electronic components 231 through 237 is located on the rotation axis Z.

Figure 3A:
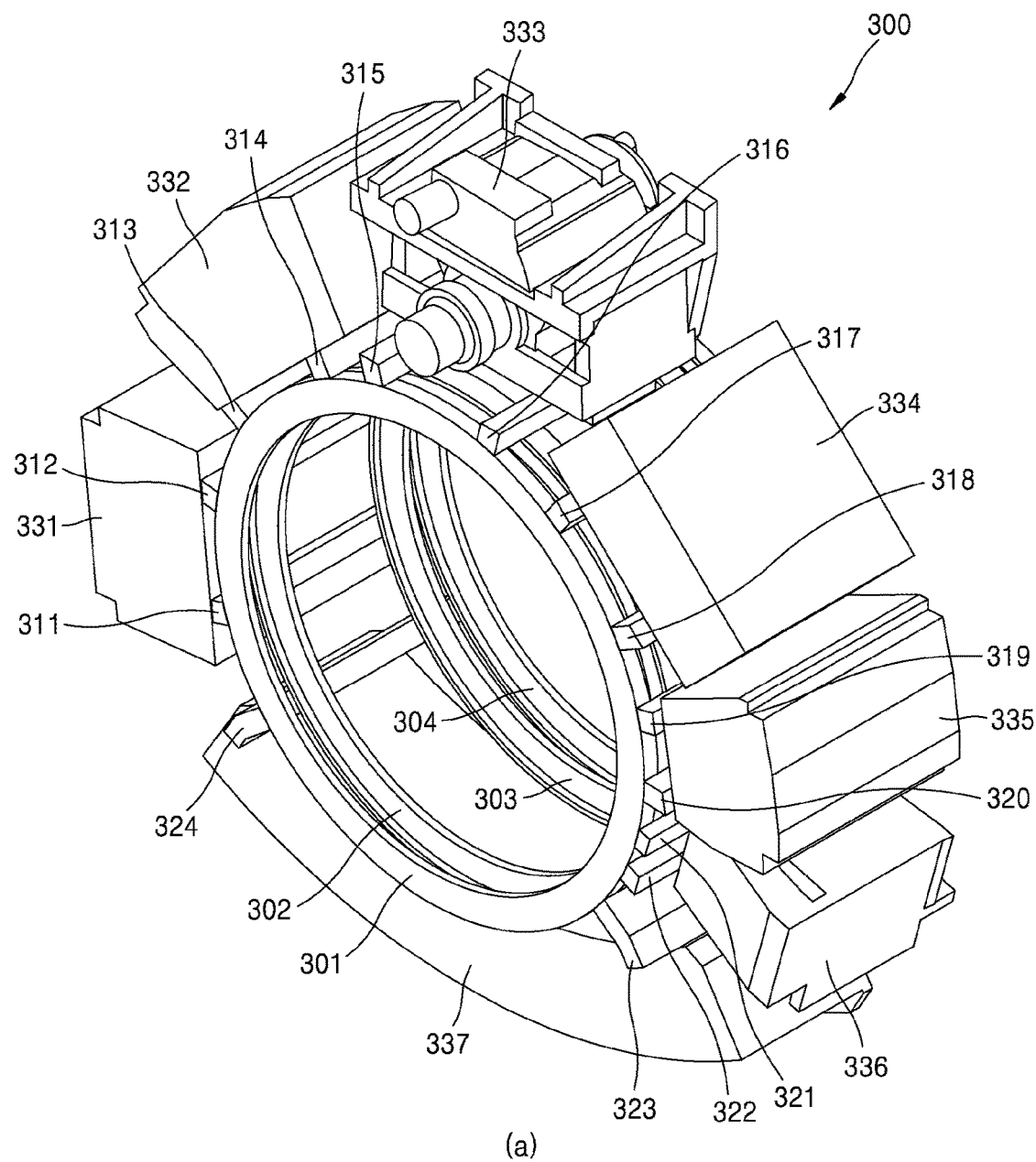
Figure 3B:
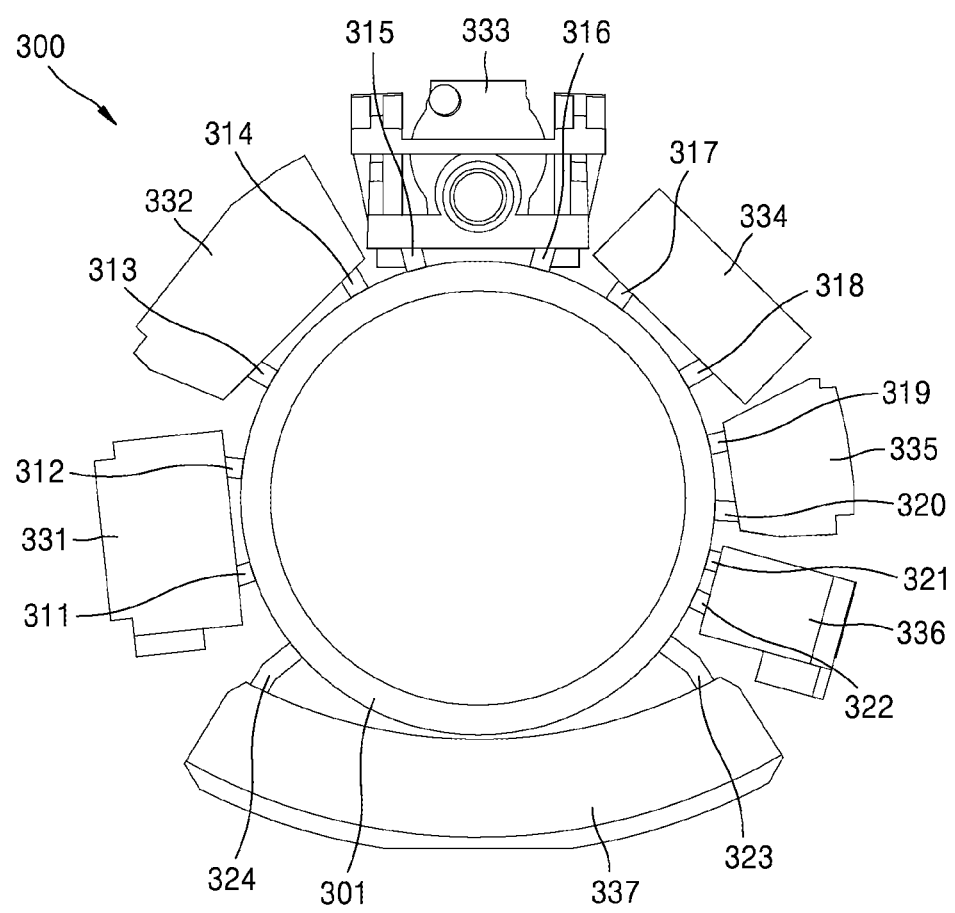
Figure 3C:
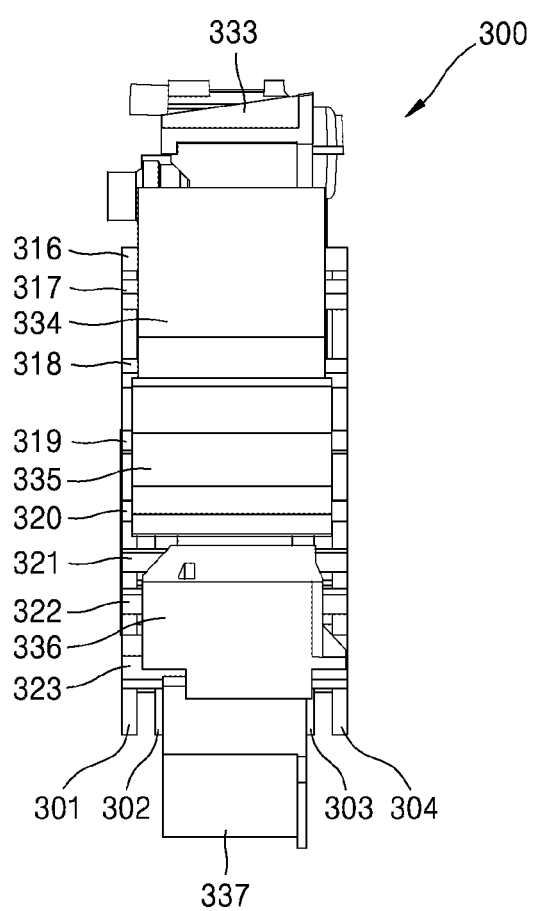

FIGS. 3A through 3C illustrate the rotating frame 300 having electronic components 331 through 337 mounted thereto as another example of the rotating frame 111 of FIG. 1. FIGS. 3A through 3C respectively illustrate a perspective view, a front view, and a side view of the rotating frame 300.

Referring to FIGS. 3A through 3C, the rotating frame 300 may include a plurality of annular frames 301 through 304 and a plurality of rib frames 311 through 324.

The plurality of rib frames 311 through 324 may be positioned on circumferential surfaces, which are oriented toward a radial direction, among surfaces of the plurality of annular frames 301 through 304. The rib frames 311 through 324 may be located on the circumferential surfaces at equally spaced intervals or in consideration of positions where the electronic components 331 through 337 are installed. In this case, the electronic components 331 through 337 may be fixedly mounted on surfaces of the rib frames 311 through 324 connecting the annular frames 301 through 304.

Figure 4A:
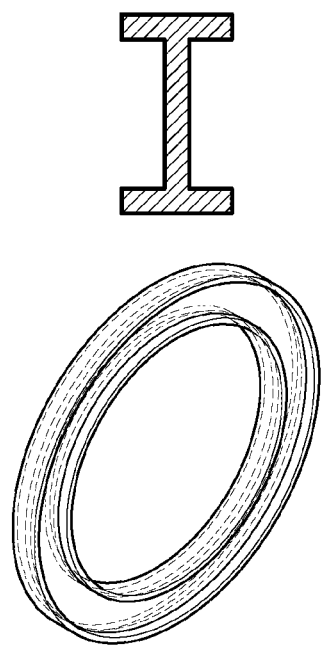
FIGS. 4A through 4C illustrate annular frames according to embodiments.
Figure 4B:
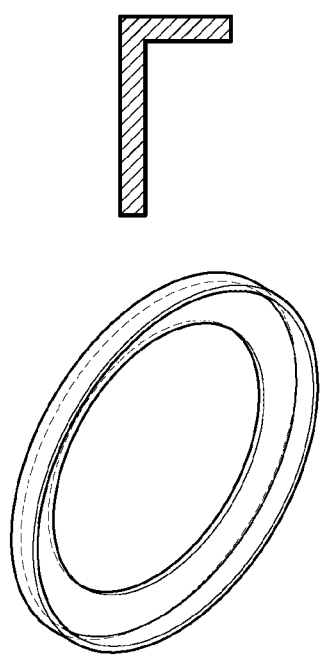
Figure 4C:
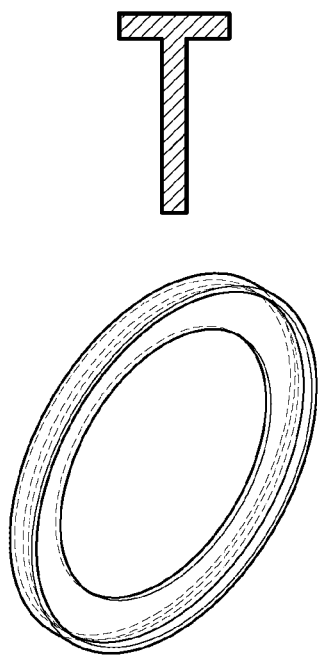

FIGS. 4A through 4C illustrate annular frames (e.g., the outer and inner annular frames 201 through 206 of FIGS. 2A through 2C and the annular frames 301 through 304 of FIGS. 3A through 3C) and cross-sections of the annular frames, according to embodiments.

An annular frame may have a recessed shape along a longitudinal direction thereof. In this case, the longitudinal direction may be a circumferential direction of the annular frame.

An annular frame having a recessed shape may have an I-shaped cross-section, as shown in FIG. 4A, an L-shaped cross-section as shown in FIG. 4B, or a T-shaped cross-section as shown in FIG. 4C. As another example, the annular frame may have a cross-section of an H-shape, a quadrilateral with a hollow central portion, or a circular shape. Furthermore, the annular frame may have a cross-section of a symmetrical L-shape.

Figure 5A:
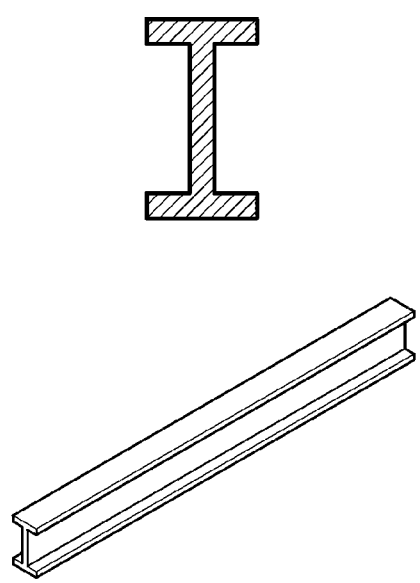
FIGS. 5A through 5C illustrate rib frames according to embodiments.
Figure 5B:
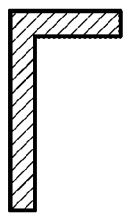
Figure 5B:
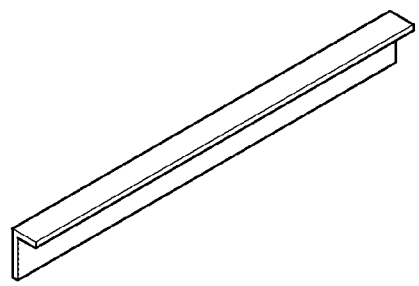
Figure 5C:
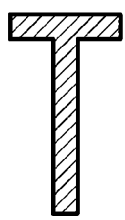
Figure 5C:
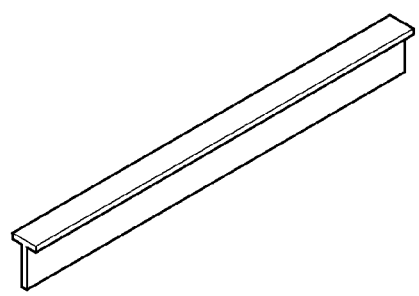

FIGS. 5A through 5C illustrate rib frames (e.g., the rib frames 211 through 224 of FIGS. 2A through 2C and 311 through 324 of FIGS. 3A through 3C) and cross-sections of the rib frames, according to embodiments.

A rib frame may have a recessed shape along a longitudinal direction thereof. The longitudinal direction may be a long-side direction of the rib frame.

A rib frame having a recessed shape may have an I-shaped cross-section as shown in FIG. 5A, an L-shaped cross-section as shown in FIG. 5B, or a T-shaped cross-section as shown in FIG. 5C. As another example, the rib frame may have a cross-section of an H-shape, a quadrilateral with a hollow central portion, or a circular shape. Furthermore, the rib frame may have a cross-section of a symmetrical L-shape.

In addition, at least a portion of a recessed space in an annular or rib frame of FIGS. 4A through 4C and FIGS. 5A through 5C may include a reinforcement made of a different material than and having lower content than that of the annular or rib frame. When the annular or rib frame is a metal die cast frame (e.g., aluminum die cast frame), the reinforcement of a different material may be a metal die cast having lower content of metal than that of the annular or rib frame, or polymer member (e.g., made of a plastic material).

Furthermore, since an annular or rib frame having a recessed shape described with reference to FIGS. 4A through 4C and FIGS. 5A through 5C has a lower strain rate than a plate-shaped frame, the annular or rib frame may further strengthen the rigidity of the gantry 110.

FIGS. 6A and 6B and 7A and 7B are diagrams illustrating structures in which rib frames and electronic components are installed, according to embodiments.

Figure 6A:
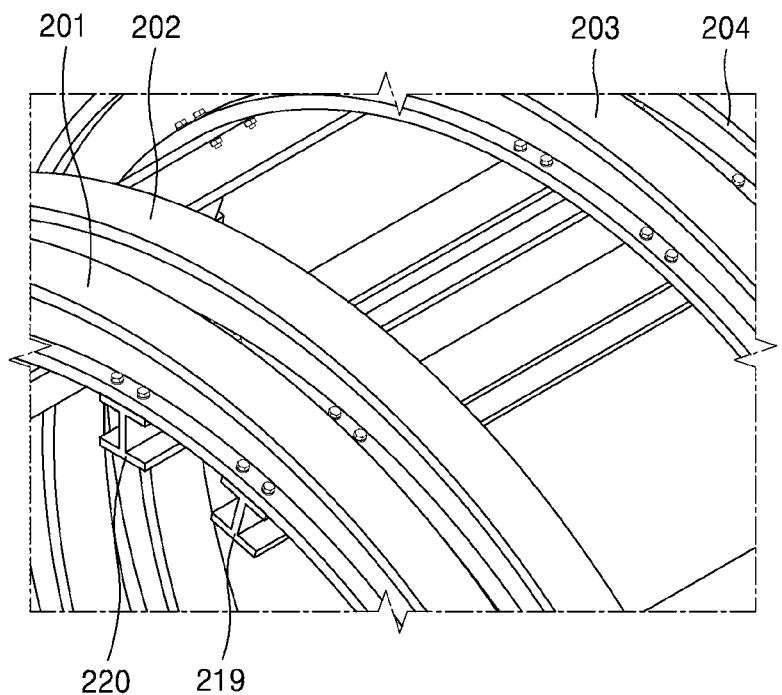
FIGS. 6A and 6B and 7A and 7B illustrate structures in which rib frames and electronic components are installed, according to embodiments.
Figure 6B:
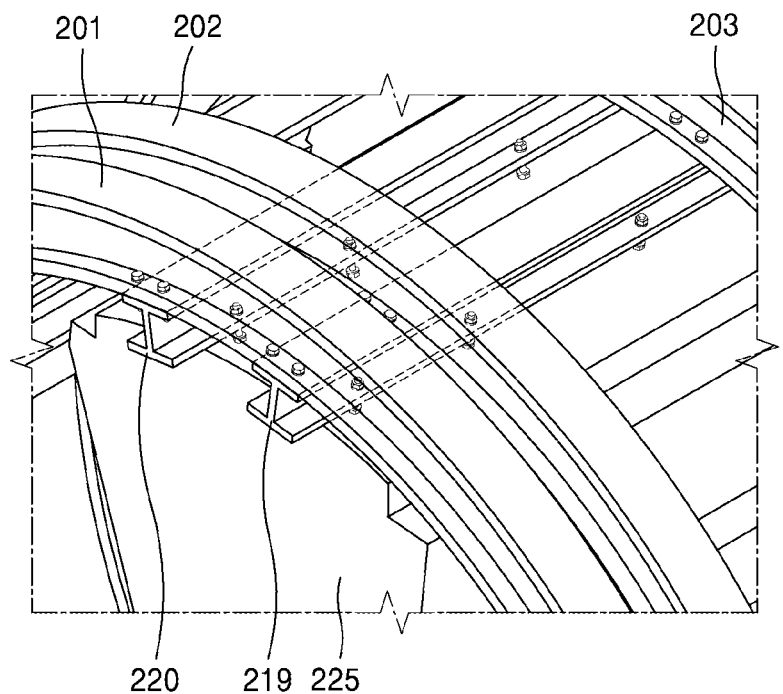

FIGS. 6A and 6B illustrate a structure in which a plurality of rib frames 219 and 220 (e.g., the rib frames 219 and 220 of FIGS. 2A through 2C) and an electronic component 225 (e.g., the electronic component 225 of FIGS. 2A through 2C) are provided on a plurality of circumferential surfaces that are oriented toward a center from among surfaces of a plurality of annular frames 201 through 204 (e.g., the outer annular frames 201 through 204).

Referring to FIG. 6A, the rib frames 219 and 220 may be arranged over the circumferential surfaces of the annular frames 201 through 204. In this case, the annular frames 201 through 204 and the rib frames 219 and 220 may be fastened together by fasteners such as at least one bolt and at least one nut.

Referring to FIG. 6B, the electronic component 225 may be mounted on surfaces of the rib frames 219 and 220. In this case, the rib frames 219 and 220 may be fastened to a bottom surface of the electronic component 225 by using at least one bolt and at least one nut.

Figure 7A:
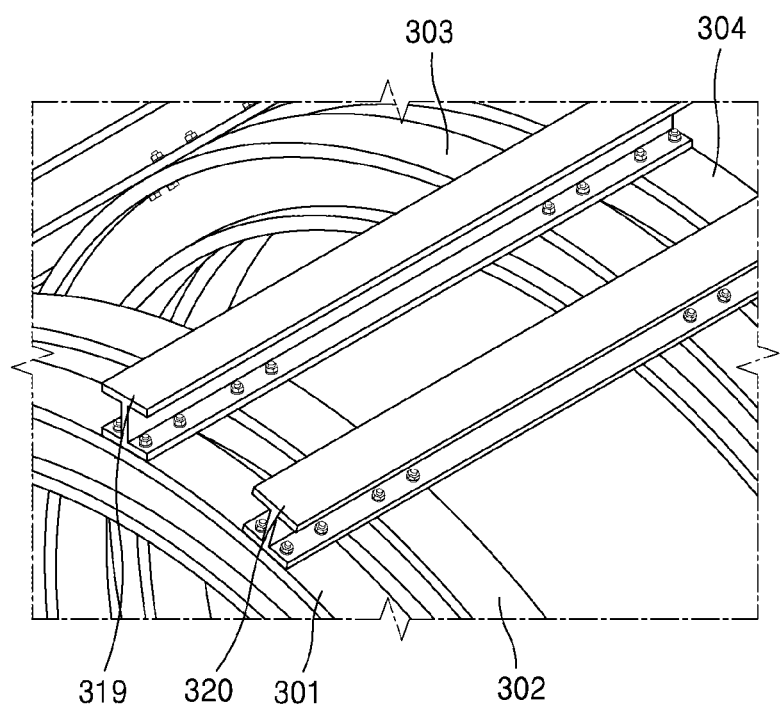
Figure 7B:
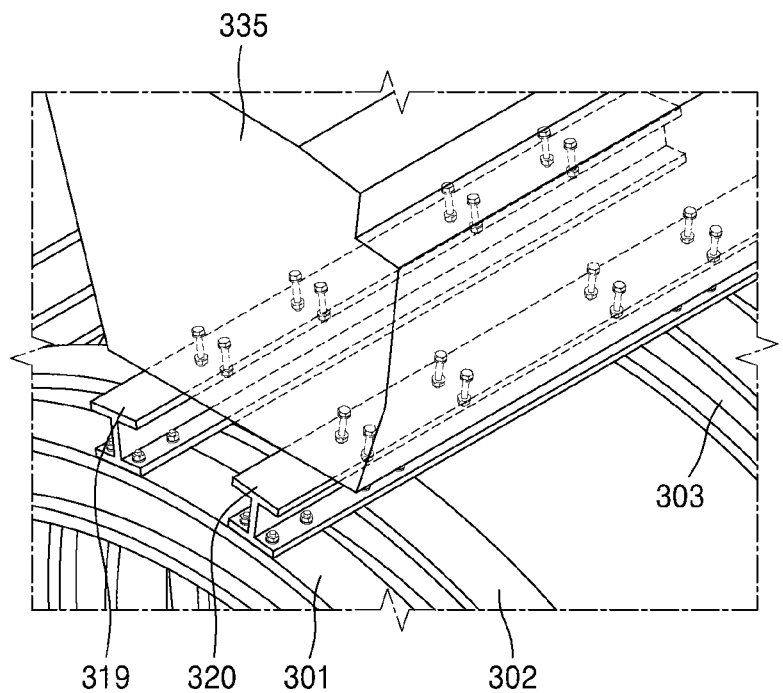

FIGS. 7A and 7B illustrate a structure in which a plurality of rib frames 319 and 320 (e.g., the rib frames 319 and 320 of FIGS. 3A through 3C) and an electronic component 335 (e.g., the electronic component 335 of FIGS. 2A through 2C) are provided on a plurality of circumferential surfaces in a radial direction from among surfaces of a plurality of annular frames 301 through 304 (e.g., the annular frames 301 through 304).

Referring to FIG. 7A, the rib frames 319 and 320 may be arranged over the circumferential surfaces of the annular frames 301 through 304. In this case, the annular frames 301 through 304 and the rib frames 319 and 320 may be fastened together by fasteners such as at least one bolt and at least one nut.

Referring to FIG. 7B, the electronic component 335 may be mounted on surfaces of the rib frames 319 and 320. In this case, the rib frames 319 and 320 may be fastened to a bottom surface of the electronic component 335 by using at least one bolt and at least one nut.

Furthermore, to strengthen the structure of engagement shown in FIGS. 6A and 6B and FIGS. 7A and 7B, contact surfaces of the annular frames 201 through 204 (301 through 304), the rib frames 219 and 220 (319 and 320), and the electronic components 225 (335) may be joined together by welding.

Figure 8A:
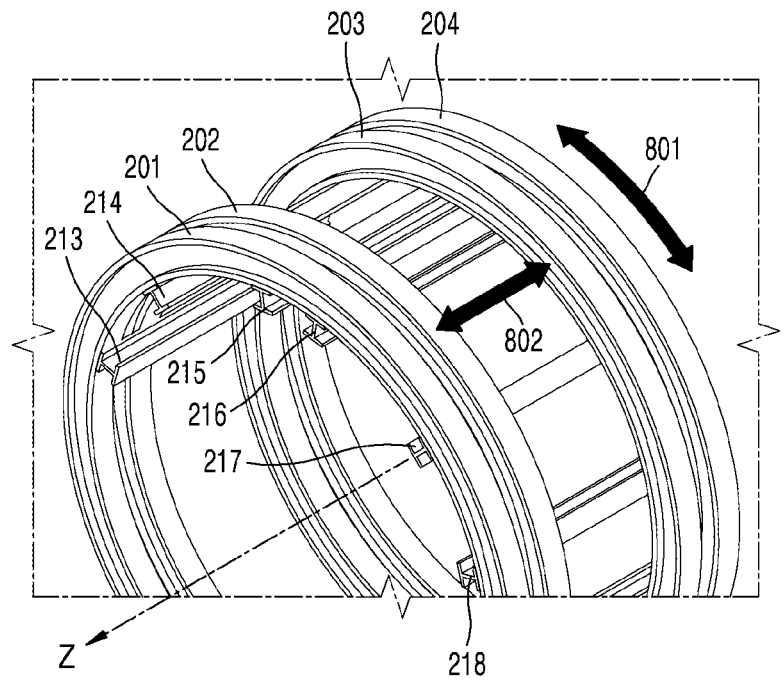
FIGS. 8A and 8B illustrate deformable rotating frames according to embodiments.
Figure 8B:
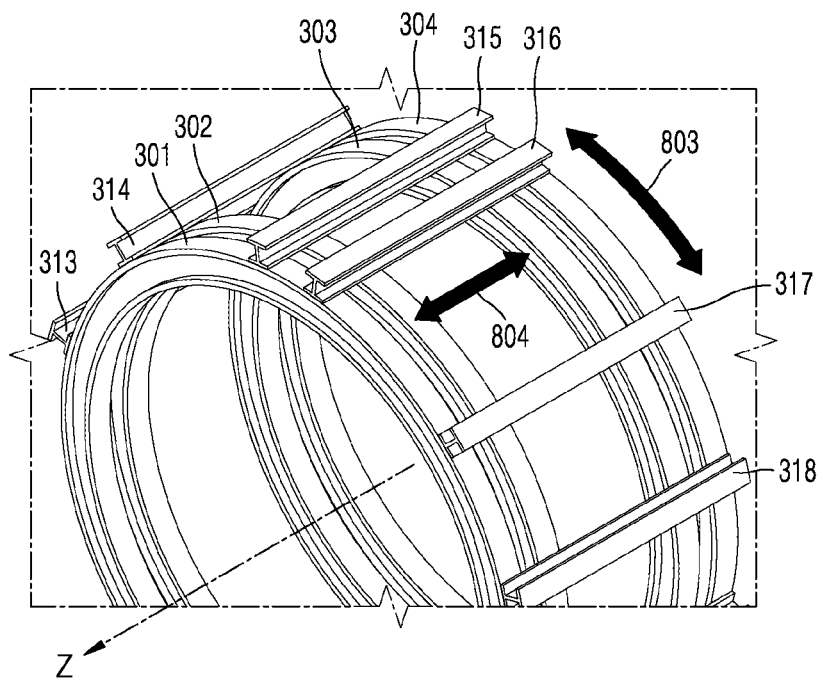

FIGS. 8A and 8B illustrate deformable rotating frames according to embodiments.

Referring to FIGS. 8A and 8B, structures of rotating frames may be deformed by spatial movement of a plurality of annular frames 201 through 204 and 301 through 304 (e.g., the outer annular frames 201 through 204 of FIG. 2A through 2C and the annular frames 301 through 304 of FIGS. 3A through 3C) and a plurality of rib frames 213 through 218 and 313 through 318 (e.g., the rib frames 213 through 218 of FIGS. 2A through 2C and 313 through 318 of FIGS. 3A through 3C).

For example, as indicated by 801 (803) of FIG. 8A (8B), at least one of the rib frames 213 through 218 (313 through 318) is movable along a circumferential direction of the annular frames 201 through 204 (301 through 304). Due to the movement, a spacing between at least two of the rib frames 213 through 218 (313 through 318) may be increased or decreased.

For example, the rib frames 213 through 218 or 313 through 318 may be moved in order to change arrangement of electronic components, enhance the rigidity of a specific portion of the rotating frame, or facilitate air flow across a specific portion of the rotating frame.

Furthermore, as indicated by 802 (804) of FIG. 8A (8B), at least one of the annular frames 201 through 204 (301 through 304) is movable along an axial direction Z. Due to the movement, a spacing between at least two of the annular frames 201 through 204 (301 through 304) may be increased or decreased.

The annular frames 201 through 204 or 301 through 304 may be moved in order to adjust a width of arrangement of electronic components, enhance the rigidity of a specific portion of the rotating frame, or facilitate air flow across the rotating frame.

In addition, to further increase the rigidity of the rotating frame shown in FIGS. 8A and 8B, the number of annular frames 201 through 204 or 301 through 304 may be further increased along the axial direction, or the number of rib frames 213 through 218 or 313 through 318 may be further increased along the circumferential direction.

Figure 9A:
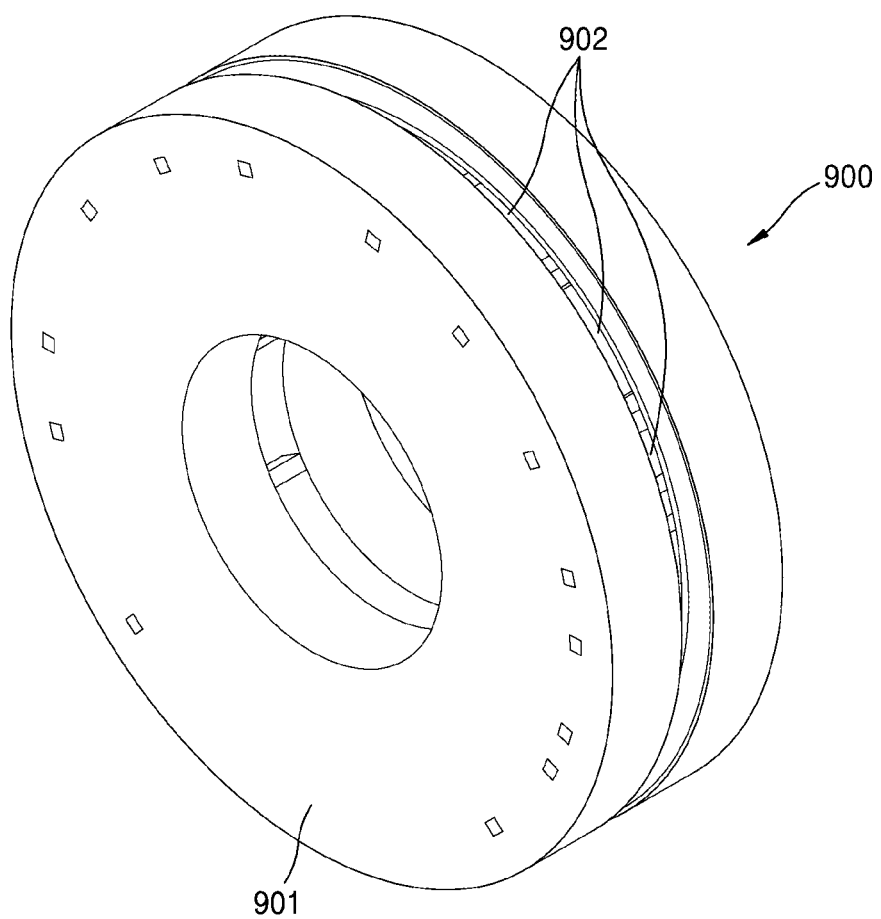
FIGS. 9A and 9B illustrate a rotating frame having a cover frame according to an embodiment.
Figure 9B:
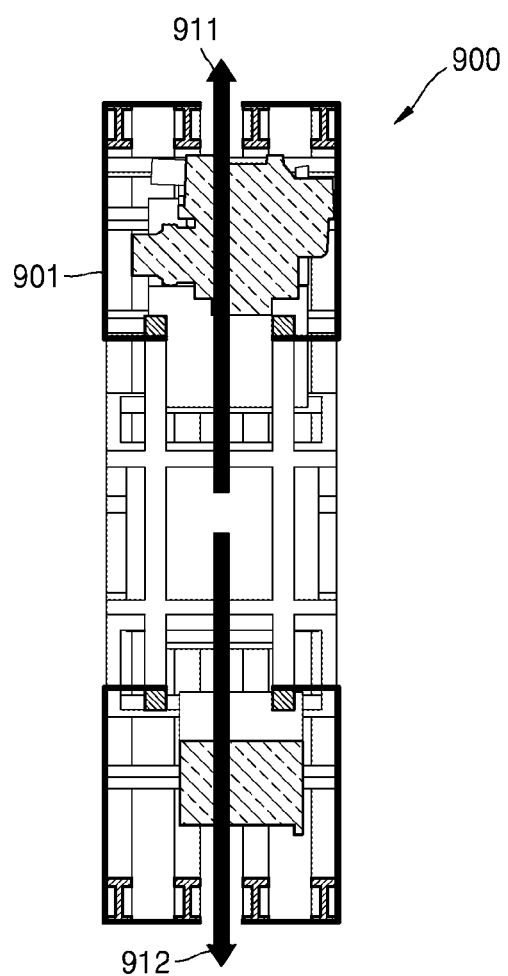

FIGS. 9A and 9B illustrate a rotating frame 900 having a cover frame 901 according to an embodiment.

Referring to FIGS. 9A and 9B, the rotating frame 900 (e.g., the rotating frame 200 of FIGS. 2A through 2C or 300 of FIGS. 3A through 3C) may be covered with the cover frame 901.

FIGS. 9A and 9B are a perspective view and a side view of the rotating frame 900 having the cover frame 901, respectively.

In this case, the cover frame 901 may include ventilation holes 902 for expelling heat generated during rotation of the rotating frame 900. In detail, heat generated within the rotating frame 900 may be expelled through spaces between annular frames and rib frames, which form the ventilation holes 902, in directions indicated by arrows 911 and 912, thereby improving the cooling efficiency of the gantry 110. Conventionally, due to a complicated structure between electronic components and rotating frames, heated air may be discharged along a circuitous path in multiple directions. However, according to embodiments, heated air may be discharged through a vertical path in a radial direction, thereby significantly improving the cooling efficiency of the gantry 110.

According to the above-described embodiments, an annular frame may have a structure similar to that of a wing of an aircraft. In other words, the annular frame may have a structure similar to that obtained when the wing of the aircraft is bent into an annular shape. In this case, a stringer extending in a longitudinal direction of the wing of the aircraft may correspond to a rotating frame according to the embodiments, while ribs extending in a transverse direction of the wing of the aircraft may correspond to rib frames according to the embodiments.

The structure similar to that of the wing of the aircraft may facilitate assembling and deformation of frames and achieve a large load and a high rigidity with light weight. For example, a gantry structure according to embodiments may provide a weight reduced by about 50%, a safety factor increased by about 20%, and a strain rate reduced by 50%, as compared to a conventional structure of a frame in a gantry having a semi-closed design.

Furthermore, an aerodynamic structure of a cover frame for covering the rotating frame may reduce the occurrence of noise and vibrations.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. A gantry of a computed tomography (CT) apparatus, the gantry comprising:
   a rotating frame configured to rotate around a rotation axis;
   a rotation driver configured to rotate the rotating frame;
   a stator configured to support the rotating frame while the rotating frame rotates; and
   electronic components arranged along a circumferential direction of the rotating frame,
   wherein the rotating frame comprises:
      a plurality of annular frames positioned concentrically around the rotation axis; and
      a plurality of rib frames arranged on circumferential surfaces of the plurality of annular frames and parallel to the rotation axis in such a manner as to connect the plurality of annular frames, and
   wherein at least one of the plurality of annular frames or the plurality of rib frames has a recessed portion along a longitudinal direction thereof.

2. The gantry of claim 1, wherein the annular frames have a recessed shape extended along a circumferential direction of the annular frames, and
   wherein the annular frames having the recessed shape have a cross-section that is one of uppercase letters I, H, T, or L or symmetrical shapes thereof.

3. The gantry of claim 1, wherein the rib frames have a recessed shape extended along a long-side direction, and
   wherein the rib frames having the recessed shape have a cross-section that is one of uppercase letters I, H, T, or L or symmetrical shapes thereof.

4. The gantry of claim 1, wherein the electronic components comprise an X-ray generator and an X-ray detector.

5. The gantry of claim 1, wherein, when the annular frames comprise a plurality of outer annular frames and a plurality of inner annular frames, the outer annular frames have a diameter greater than that of the inner annular frames.

6. The gantry of claim 1, wherein, when the annular frames comprise a plurality of outer annular frames and a plurality of inner annular frames, the rib frames are positioned on circumferential surfaces, which are oriented toward a center located on the rotation axis, among surfaces of the outer annular frames.

7. The gantry of claim 1, wherein, when the annular frames comprise a plurality of outer annular frames and a plurality of inner annular frames, the electronic components are provided between the outer and inner annular frames.

8. The gantry of claim 7, wherein the electronic components are fixedly mounted on surfaces of the rib frames connecting the outer annular frames.

9. The gantry of claim 1, wherein the rib frames are positioned on circumferential surfaces, which are oriented in a radial direction, among surfaces of the annular frames.

10. The gantry of claim 9, wherein the electronic components are fixedly mounted on surfaces of the rib frames connecting the annular frames.

11. The gantry of claim 1, wherein the rib frames are positioned on circumferential surfaces of the annular frames relative to the electronic components.

12. The gantry of claim 1, wherein the rib frames are movable along a circumferential direction of the annular frames.

13. The gantry of claim 1, wherein the annular frames are movable along the rotation axis.

14. The gantry of claim 1, further comprising a cover frame configured to cover the rotating frame, the cover frame includes a plurality of ventilation holes.

15. The gantry of claim 14, wherein the plurality of ventilation holes are arranged to discharge air heated in the gantry in a radial direction.

16. The gantry of claim 1, wherein the recessed portion comprises a reinforcement made of a different material than and having lower content than that of the at least one of the annular frames and the rib frames.

17. The gantry of claim 1, wherein the annular frames and the rib frames are fastened together by fasteners including a bolt and a nut.

18. The gantry of claim 1, wherein the electronic components and the rib frames are fastened together by fasteners including a bolt and nut.

19. The gantry of claim 1, wherein the electronic components comprise a plurality of X-ray generators and a plurality of X-ray detectors.

20. The gantry of claim 1, wherein the plurality of rib frames arranged on the circumferential surfaces are arranged at equally spaced intervals.

* * * * *